US00PP17387P3

(12) United States Plant Patent
White

(10) Patent No.: US PP17,387 P3
(45) Date of Patent: Jan. 30, 2007

(54) PEAR TREE NAMED 'PREM2P'

(50) Latin Name: ***Pyrus communis*×*Pyrus pyrifolia***
Varietal Denomination: 'Prem2P'

(75) Inventor: Allan G White, Havelock North (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 10/900,689

(22) Filed: Jul. 27, 2004

(65) Prior Publication Data

US 2006/0026725 P1 Feb. 2, 2006

(51) Int. Cl.
*A01H 5/00* (2006.01)

(52) U.S. Cl. ..... Plt./176
(58) Field of Classification Search ..... Plt./176
See application file for complete search history.

(56) References Cited

PUBLICATIONS

UPOV ROM GTITM Computer Database, GTI Jouve Retrieval Software 2005/03 Citation for 'Crispie'.*
*New Zealand Plant Variety Rights Journal*, No. 75, Jul.–Sep. 1998, published Oct. 14, 1998, p. 2.
Application for Plant Variety Rights under Plant Variety Rights Act 1987 (New Zealand), filed Jul. 2, 1998.

* cited by examiner

*Primary Examiner*—Wendy Haas
(74) *Attorney, Agent, or Firm*—Stratton Ballew PLLC

(57) ABSTRACT

A new distinct pear variety is described. This interspecific variety results from crossing between 'Nijisseiki' (*Pyrus pyrifolia* Nakai) (not patented) and 'Max Red Barlett' (*Pyrus communis*) (U.S. Plant Pat. No. 741). The new variety has been named 'Prem2P' and was selected because of its crisp texture and 'Bartlett' type flavor. The fruit of this new variety is characterized by its pyriform shape, smooth yellow skin, crisp texture and 'Bartlett' type flavor when fully ripe.

9 Drawing Sheets

Genus and speces of plant claimed: *Pyrus communis*× *Pyrus pyrifolia.*
Variety denomination: 'Prem2P'.

BACKGROUND OF THE INVENTION

A new distinct pear variety is described. This interspecific variety results from crossing between 'Nijisseiki' (*Pyrus pyrifolia* Nakai) (unpatented) and 'Max Red Barlett' (*Pyrus communis*) (U.S. Plant Pat. No. 741). The new variety has been named 'Prem2' and was selected because of its crisp texture and 'Bartlett' type flavour. The fruit of this new variety is characterised by its pyriform shape, smooth yellow skin, crisp texture and 'Bartlett' type flavour when fully ripe.

SUMMARY OF THE INVENTION

This new variety of pear (*Pyrus* hybrid) was created in the course of a planned breeding program, carried out in Hawkes Bay, New Zealand. The parents used to make the cross, in 1989, were 'Nijisseiki' (seed parent) and 'Max Red Bartlett' (pollen parent). 'Prem2P' arose from a single plant selected from a population of seedlings derived from the parents listed above. The tree was chosen because of its fruit which have an attractive pyriform shape, crisp texture and 'Bartlett' flavour when ripe. The variety was determined to be distinct from the parent varieties by the following characteristics:

Nijisseiki (*Pyrus pyrifolia* Nakai) (unpatented): 'Prem2P' has strong tree vigour compared to medium vigour of 'Nijisseiki', pyriform fruit shape compared to the round shape of 'Nijisseiki', 'Bartlett' like flavour when fully ripe compared to a mild subtle flavour of 'Nijisseiki'.

Max Red Bartlett (*Pyrus communis*) (U.S. Plant Pat. No. 741): The tree of 'Prem2P' is vigorous compared to medium vigour of 'Max Red Bartlett'. 'Prem2P' fruits on spurs and heavily on one year old wood while 'Max Red Bartlett' fruits mostly on spurs. 'Prem2P' fruit has yellow skin colour when ripe and firm crisp texture compared to the red skin colour of 'Max Red Bartlett' and soft texture.

Williams' Bon Chretien (*Pyrus communis*) (unpatented): The tree of 'Prem2P' is vigorous compared to medium vigour of 'Williams' Bon Chretien'. 'Prem2P' fruits on spurs and heavily on one year old wood while 'Williams' Bon Chretien' fruits mostly on spurs. 'Prem2P' fruit has a narrow calyx end shape when compared with 'Williams' Bon Chretien'. 'Prem2P' has firm crisp texture compared to the soft texture of 'Williams' Bon Chretien'.

The new variety has been named 'Prem2P'. True to type budding and grafting onto Quince rootstock 'BA29' (unpatented) with 'Buerre Hardy' (unpatented) pear as an interstock has been used to obtain plants. Asexual propagation by budding and grafting has shown that the unique combinations of characteristics are consistently transferred through successive propagation.

BRIEF DESCRIPTION OF THE DRAWINGS

The accompanying photographs show typical specimens of the tree, foliage, fruit of the new variety as depicted in colours nearly as true as is reasonably possible to make the same colour illustration of this character.

MORPHOLOGICAL DESCRIPTION OF THE VARIETY

Figure 1:
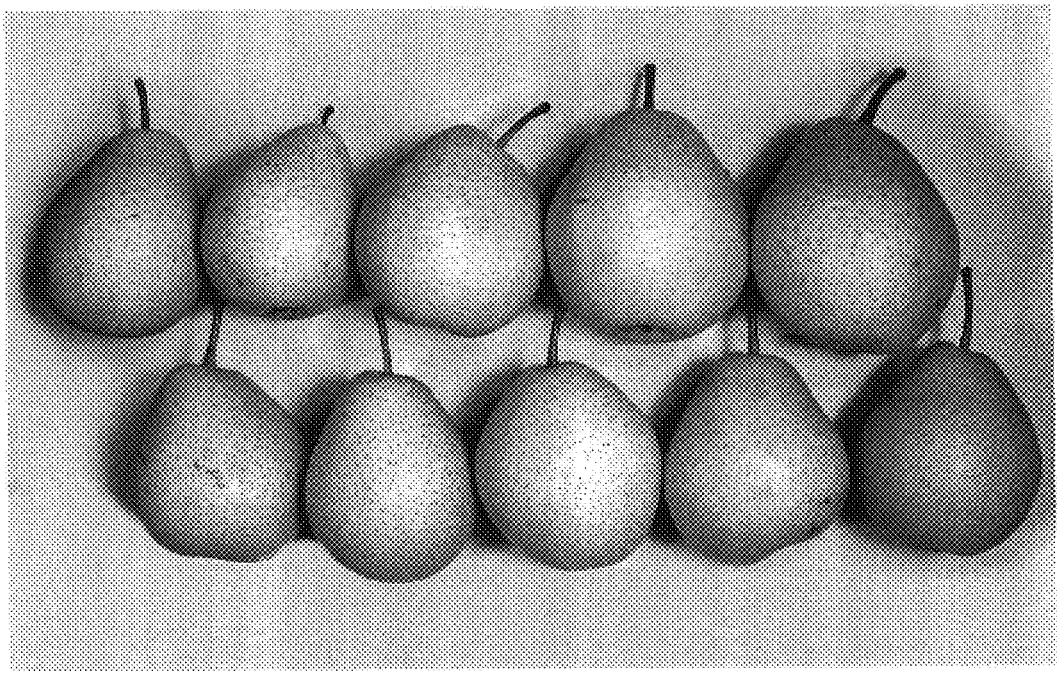
FIG. 1: side view of typical fruit of the pear variety 'Prem2P'.
Figure 2:
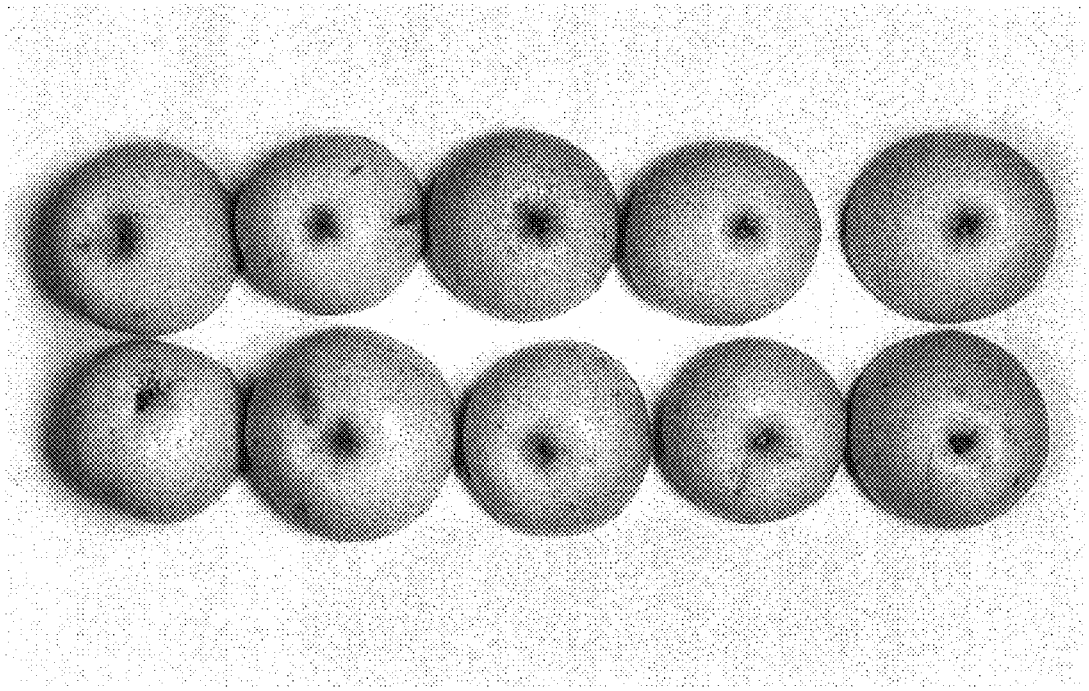
FIG. 2: calyx end view of typical fruit of the pear variety 'Prem2P'.
Figure 3:
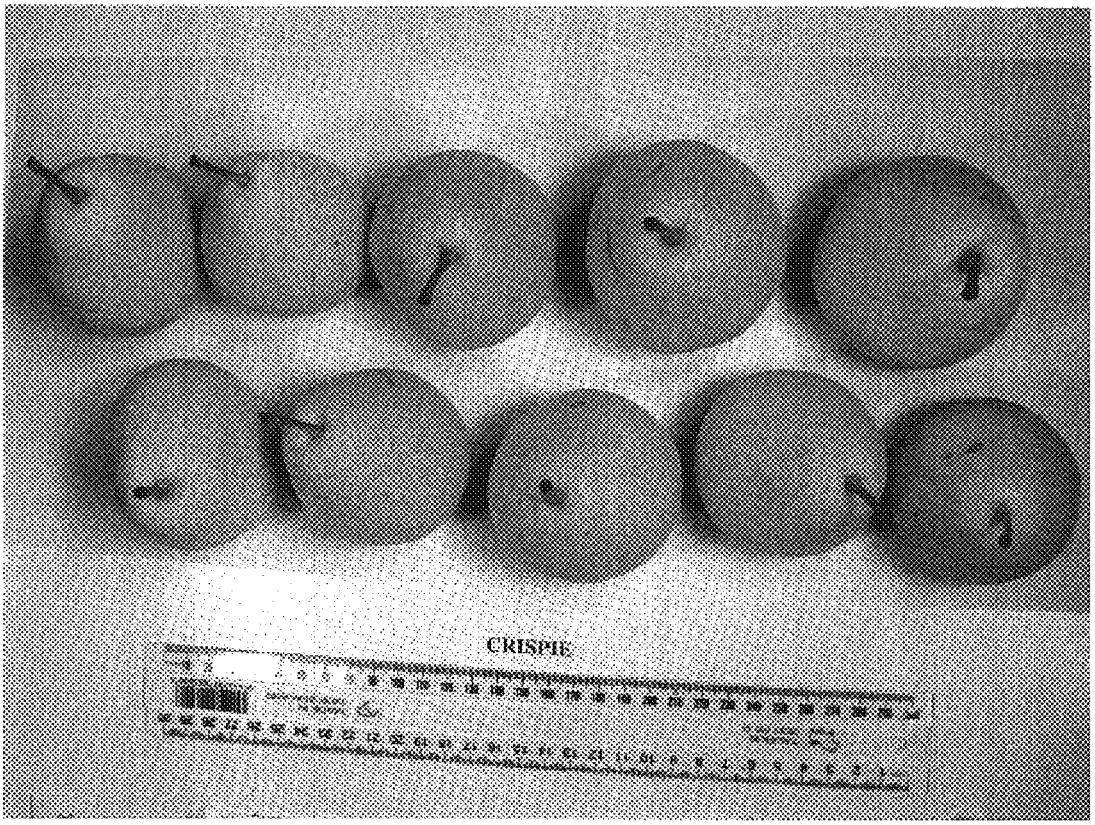
FIG. 3: stem end view of a typical fruit of the pear variety 'Prem2P'.
Figure 4:
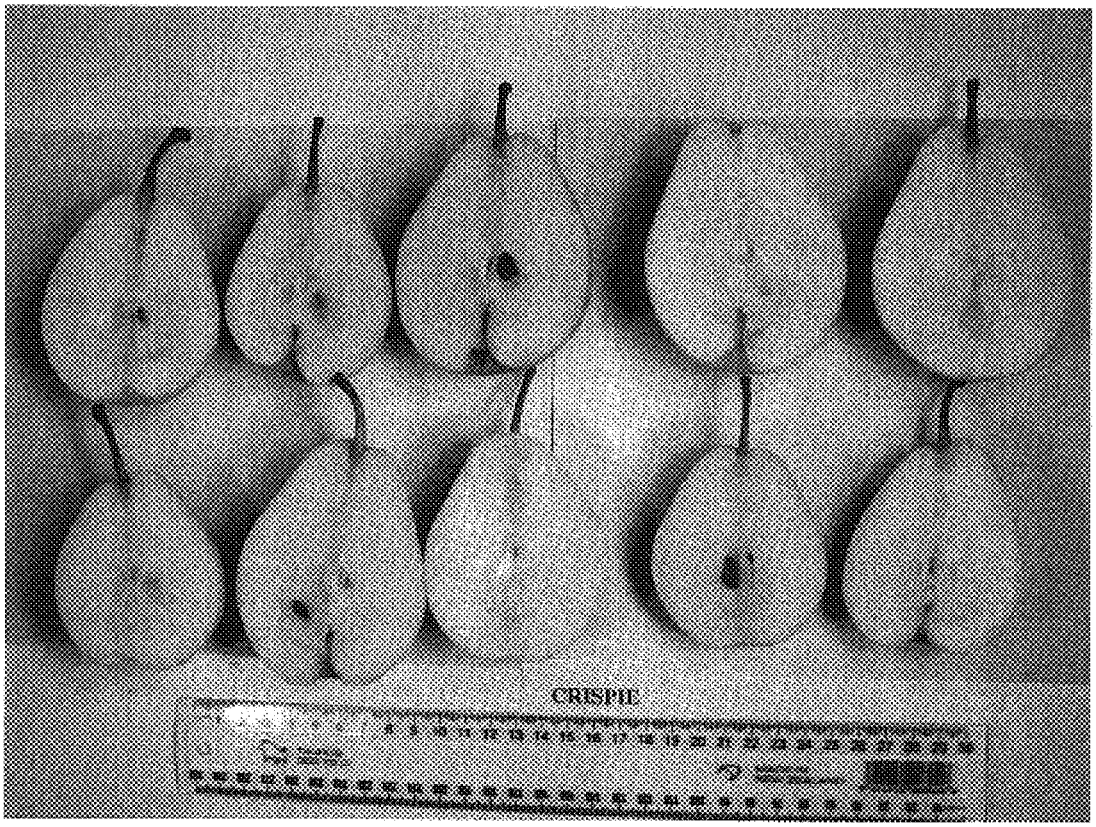
FIG. 4: cross sectional view of a typical fruit of the pear variety 'Prem2P'.
Figure 5:
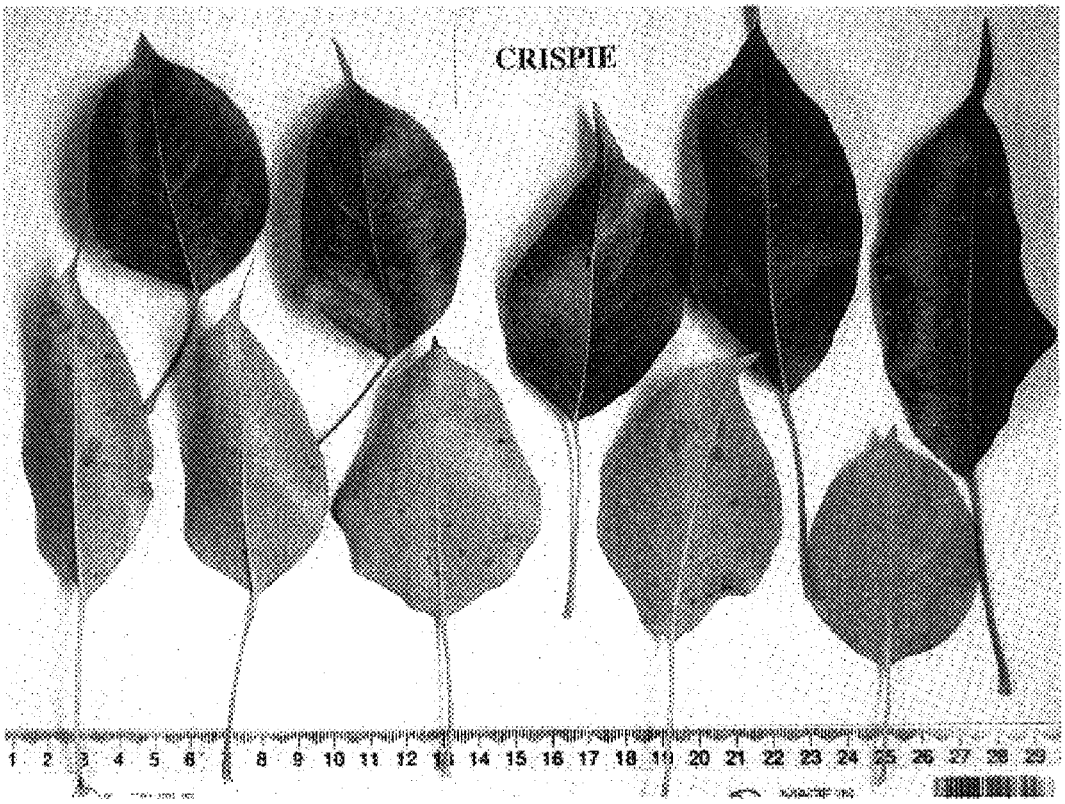
FIG. 5: typical mature leaves of 'Prem2P' showing the upper and lower surfaces.
Figure 6:
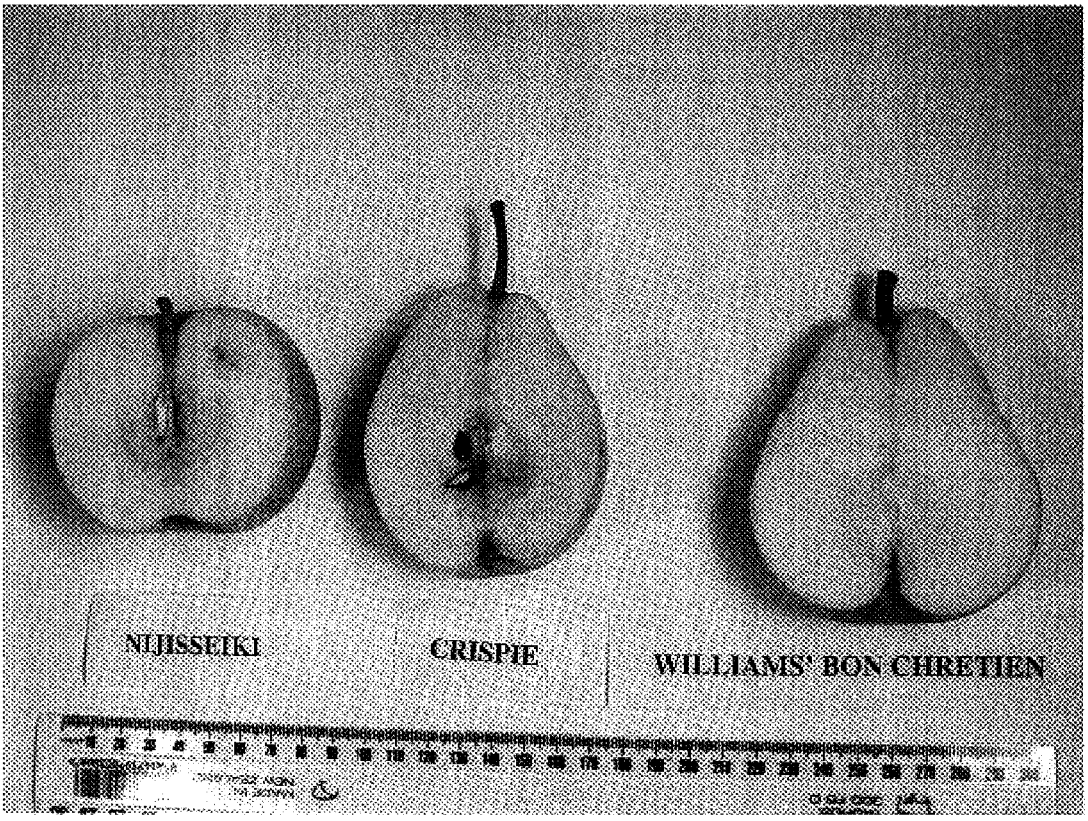
FIG. 6: cross sectional fruit view of 'Nijisseiki', (far left), 'Prem2P' (middle), 'Williams' Bon Chretien' (right).
Figure 7:
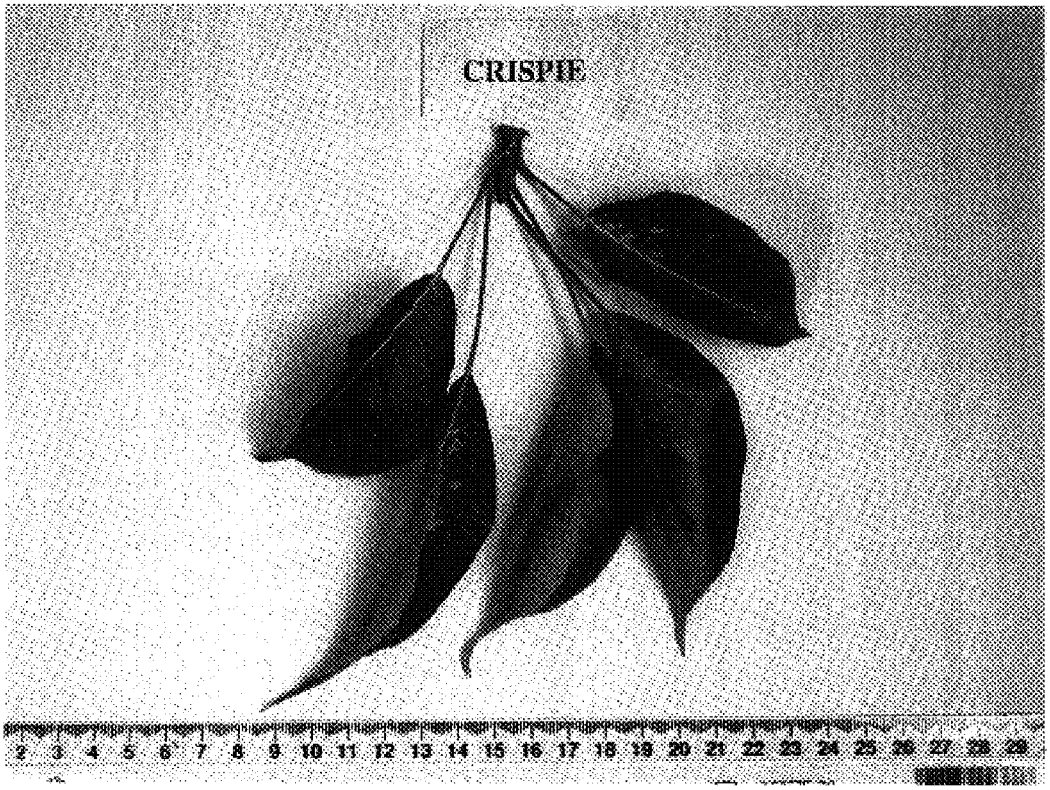
FIG. 7: fruiting spur 'Prem2P'.
Figure 8:
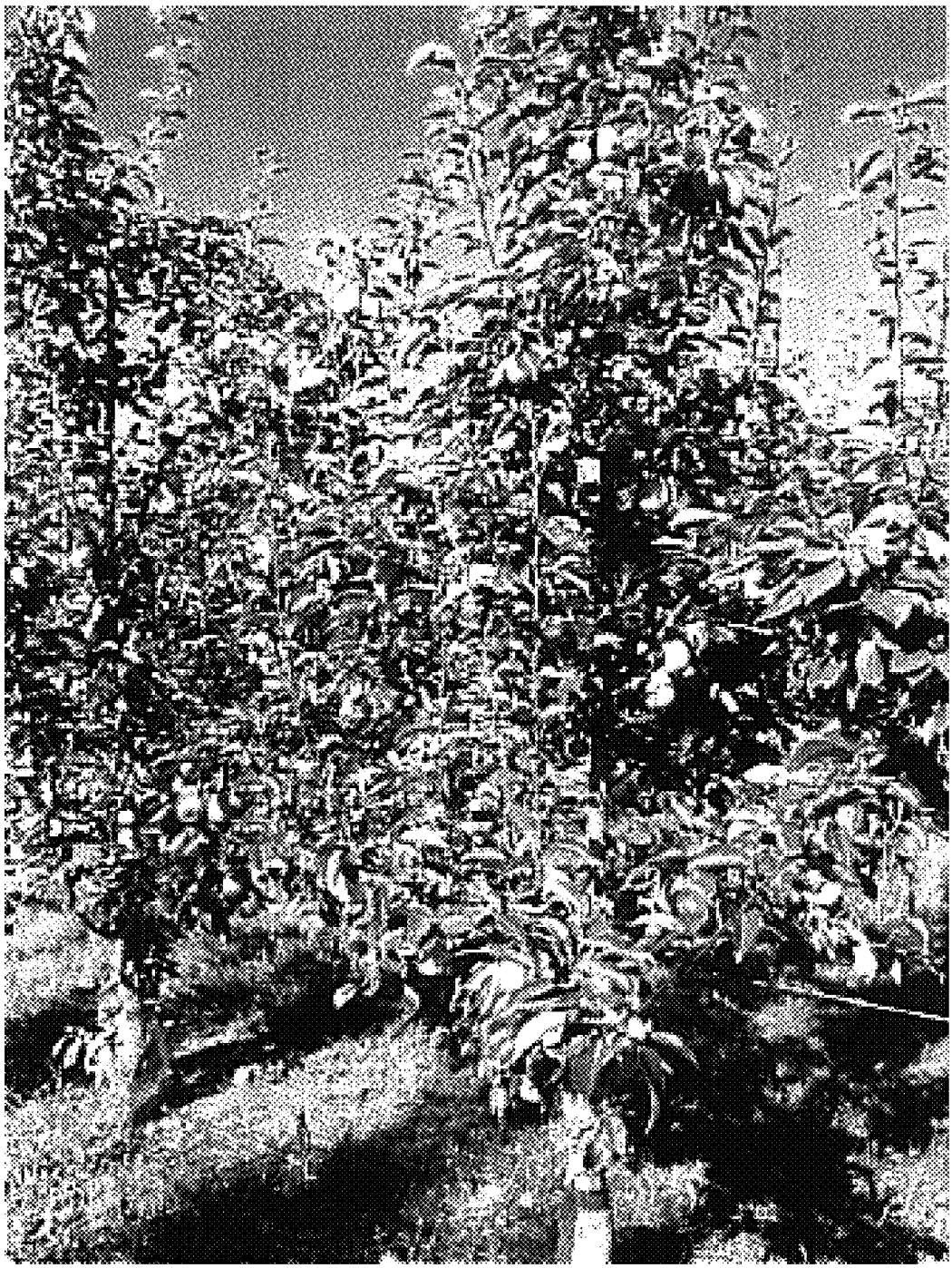
FIG. 8: tree of variety 'Prem2P'.
Figure 9:
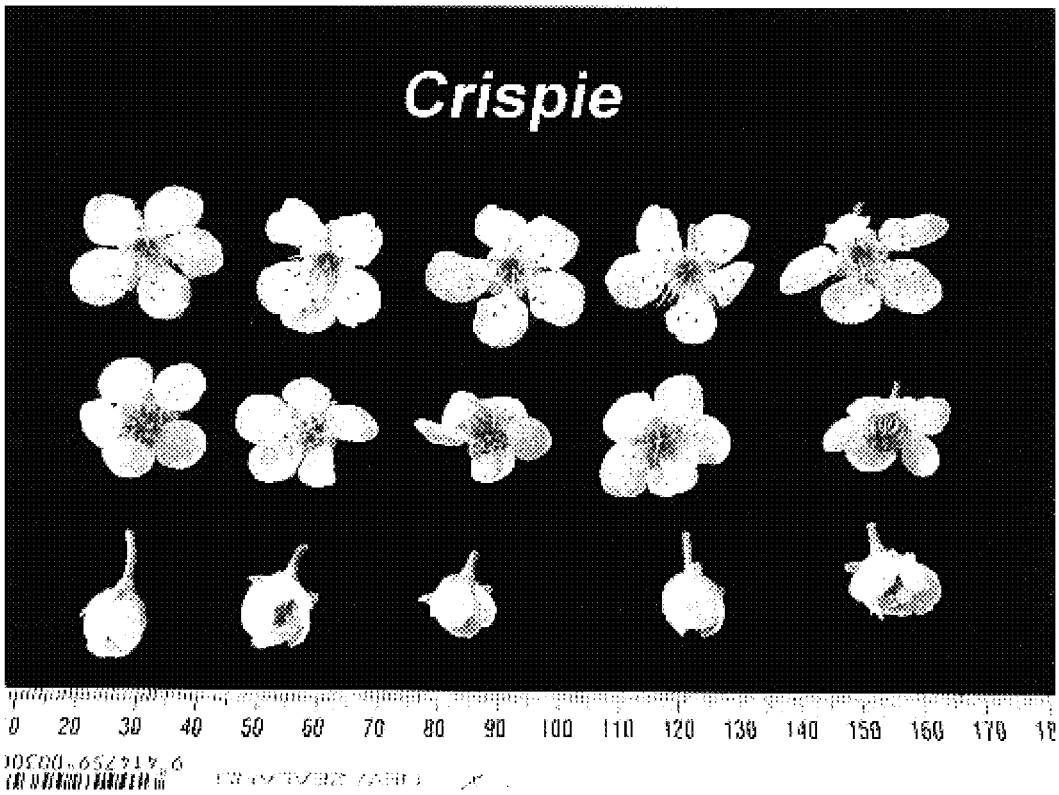
FIG. 9: flowers and flower buds of 'Prem2P'.

The following is a detailed description of the new variety with colour terminology in accordance with The Royal Horticultural Society Colour Charts (R.H.S.C.C.) 2001 edition.

Observations were made on four year old trees grafted onto Quince 'BA29' rootstocks with a 'Buerre Hardy' pear interstock, planted in 1999 at Nelson, New Zealand (173°0' E. 41°4' S.). Climatic conditions in the Nelson area are temperate with an average rainfall of 1300 mm and over 2,500 sunshine hours per year.

Tree: Vigour strong when grafted onto Quince 'BA29' rootstocks with a 'Buerre Hardy' interstock; tree size large, height 4.2 m, diameter 3.06 m; branching strong; habit spreading, crotch angles range from 20° to 50° and average 35.4°; bearing fruit on spurs and 1 year wood.

Trunk: Bark grey R.H.S.C.C. N200D, smooth, no cracking when mature; trunk circumference of 218 mm at a height of 200 mm.

Branches: Strong; number high, average 4.5 lower tier branches, average 41.4 mm in diameter and 5 upper tier branches, average 29.5 mm in diameter on pruned centre leader trees; approximately 3 spurs/100 mm on 2 year old wood; high annual growth numbers with a length of 400–500 mm; annual growth wood is greyed orange R.H.S.C.C. 166A.

Lenticels: Numbers on current years growth medium 4 per 10 $mm^2$; size large, length 1.8 mm, width 1.1 mm; colour greyed yellow R.H.S.C.C. 161D. Lenticels are also present on one and two year old branches. Lenticel prominence fades on wood older than 2 years and are not conspicuous on the trunk.

Leaves: Average length 103.5 mm; width 60.2 mm; average length / width ratio medium; upward pose; shape in cross section up folded; indentations of the margin sharply serrate, medium depth; shape of leaf blade apex (excluding pointed tip) right angled; shape of leaf base obtuse; petiole average length 38.1 mm, diameter 1.5 mm; petiole colour on upper side R.H.S.C.C. 4A, petiole colour on lower side R.H.S.C.C. 2C; stipules absent; colour of upper surface of leaf blade green R.H.S.C.C. 146A, colour of lower leaf blade surface yellow-green R.H.S.C.C. 147B.

Flower buds: Flower bud length medium (average 12 mm), diameter (average 11.7 mm); colour white R.H.S.C.C. 155B.

Flowers: Bloom period medium late, from September $24^{th}$ to October $15^{th}$ in Nelson, New Zealand, full bloom date October $4^{th}$ ; sepal length medium; sepal attitude in relation to the corolla recurved; flower width (average 23.3 mm); depth 8.9 mm; margins of petals overlapping; position of stigma in relation to stamens same level; size of petal medium; shape of petal (excluding claw) circular; shape of petal base (excluding claw) cuneate; petal number predominantly 5 but occasionally 6; petal length (average 10.3 mm); petal width (average 10.7 mm); petal colour white R.H.S.C.C. 155B; length of claw petal short; style number 5.

Fruit: Fruit is mature for consumption by the third week of February; harvest period is from February 10 to February 20, in Nelson, New Zealand. Average penetrometer readings measured on the February $18^{th}$ 2003 were 5.1 N. in Nelson and 4.2 N. in Hawkes Bay, Brix 9.8 in Nelson and 11.2 in Hawkes Bay New Zealand.

Size: Medium large; average fruit weight 214.8 g; average width 71.1 mm, average height 85.6 mm; fruit length / diameter ratio medium; maximum diameter slightly towards calyx of fruit.

Shape: Pyriform; slightly asymmetric in longitudinal section; profile of the sides straight.

Eye basin: Average width 24.5 mm; average depth 4.9 mm, relative area of russet around eye basin very small.

Stalk: Thickness of the stalk medium, medium length 21.7 mm, curvature of stalk weak to medium, the attitude of the stalk is oblique in relation to the axis of the fruit; depth of stalk cavity shallow average 2.6 mm, amount of russet around the stem cavity small.

Sepal: Calyx or sepals are partially persistent, approximately 10% of fruit at harvest have a deciduous calyx and sepals, remaining 90% have upright sepals.

Skin: Smooth; greasiness absent, cracking tendency of skin absent; background colour yellow R.H.S.C.C. 8B; lenticels small.

Overcolour: Absent.

Texture: Crisp; flesh medium; firmness medium; flesh juiciness medium.

Flavour: Sweetness medium; acidity low; 'Bartlett' like aroma when ripe.

Quality: Fruit of 'Prem2P' harvested on February $16^{th}$ in Nelson, New Zealand and stored for one month at 0.5° C. followed by seven days at 20° C., continued to display good eating quality.

Seeds: Five locules, 1 to 2 seeds per locule; medium seed size 11 mm long, 5 mm wide, colour black R.H.S.C.C. 202A.

Use: Dessert.

Production: Early season, regular cropping when thinned.

Management: Thinning of crop load in early summer is recommended. Early cropping is required to keep vegetative growth in balance.

Pest and disease: Susceptible to pear slug (*Caliroa cerasi*). Highly leaf and fruit resistant to pear scab)*Venturia pirina* Adherh).

I claim:

1. A new and distinct variety of pear tree named 'Prem2P' substantially as herein illustrated and described.

* * * * *